United States Patent [19]

Audette

[11] Patent Number: 4,821,707

[45] Date of Patent: Apr. 18, 1989

[54] MECHANICAL ARTICULATED JOINT FOR KNEE BRACES

[76] Inventor: André Audette, 172, Avenue Breton, Laval-des-Rapides, (Quebec), Canada, H7N 3L1

[21] Appl. No.: 138,075

[22] Filed: Dec. 28, 1987

[51] Int. Cl.$^4$ .......................... A61F 5/01; A61F 5/04
[52] U.S. Cl. ............................ 128/80 F; 128/80 C; 623/39
[58] Field of Search ................ 128/80 F, 80 C, 80 R, 128/88; 623/39

[56] References Cited

U.S. PATENT DOCUMENTS

| | | | |
|---|---|---|---|
| 575,199 | 1/1897 | Autenrieth . | |
| 1,092,836 | 4/1914 | Hart . | |
| 2,883,982 | 4/1959 | Rainey | 128/80 |
| 3,387,305 | 6/1968 | Shafer | 2/22 |
| 3,669,105 | 6/1972 | Castiglia | 128/80 C |
| 3,901,223 | 8/1975 | May | 128/80 F |
| 3,902,482 | 9/1975 | Taylor | 128/80 F |
| 4,256,097 | 3/1981 | Willis | 128/80 C |
| 4,523,585 | 6/1985 | Lamb et al. | 128/80 C |
| 4,628,916 | 12/1986 | Lerman et al. | 128/80 C |
| 4,715,363 | 12/1987 | Detty | 128/80 C |

FOREIGN PATENT DOCUMENTS

| | | |
|---|---|---|
| 885574 | 11/1971 | Canada . |
| 1007121 | 3/1977 | Canada . |
| 1011204 | 5/1977 | Canada . |
| 1017641 | 9/1977 | Canada . |
| 1063899 | 10/1979 | Canada . |
| 1091114 | 12/1980 | Canada . |
| 1120811 | 3/1982 | Canada . |
| 1201951 | 3/1986 | Canada . |

OTHER PUBLICATIONS

De Puy, A Division of Boehringer Mannheim Corporation, "Alignment Procedure".
1. Townsend- 2. Polycentric MTP- 3. Polycentric- 4. Single Pivot- 5. Polycentric Condylar Gears- 6. Poly-Axial- 7. Mult-Centric- 8. Preload.
"The Iowa Knee Orthosis", Donald Shurr et al.
"A New Concept in Orthotics—The Northwestern University Knee Orthosis System", Jack L. Lewis et al., pp. 18–19.
"The ACL Dilemma Finally Tackled . . . ", Townsend Industries, Inc.
"The Genucentric Knee Orthosis—A New Concept", Robert Foster et al, Orthotics and Prosthetics, vol. 33, No. 2, pp. 31–43, Jun. 1979.
The Polyaction Knee Orthosis, Becker Orthopedic (1983).
"Becker Orthopedic Presents The Polyaction Knee Orthosis", Becker Orthopedic Appliance Company.
Orthotics & Prosthetics, Sep. 1971, pp. 2–6.
Orthotics Components and Systems, "The Lower Limb", pp. 217–218.
VAPC Prescription Procedures for KO's and KAFO's (Adult).
Brian Reed, FIG. 1.

Primary Examiner—David A. Wiecking
Assistant Examiner—Tonya Lamb
Attorney, Agent, or Firm—Foley & Lardner, Schwartz, Jeffery, Schwaab, Mack, Blumenthal & Evans

[57] ABSTRACT

An articulated mechanical joint for use in knee apparatuses such as knee braces allowing extension and flexion of the wearers' knees to which the braces are applied, artificial articulated knees of leg prostheses, and the like, comprises a pair of elongated femoral and tibial links edgedly facing each other at one end and a pair of cheek plates one on each side over the links. Each cheek plate is pivotally connected to both links up their edgedly facing ends, one plate independently of the other so that each end of each link has two pivots connecting to the two plates. The pivot axes of the different pivots are so positioned that the rotation axis of the pivotally connected links is so shifted as to reproduce accurately the complex rotation of the knee. Moreover, because of the strengthening cheek plates, the mechanical joint provides a better resistance to sidewise motion of the tibia and femur of the leg. The mechanical joint further includes a stop device which prevents extension and flexion of the links beyond predetermined extension and flexion limits.

20 Claims, 15 Drawing Sheets

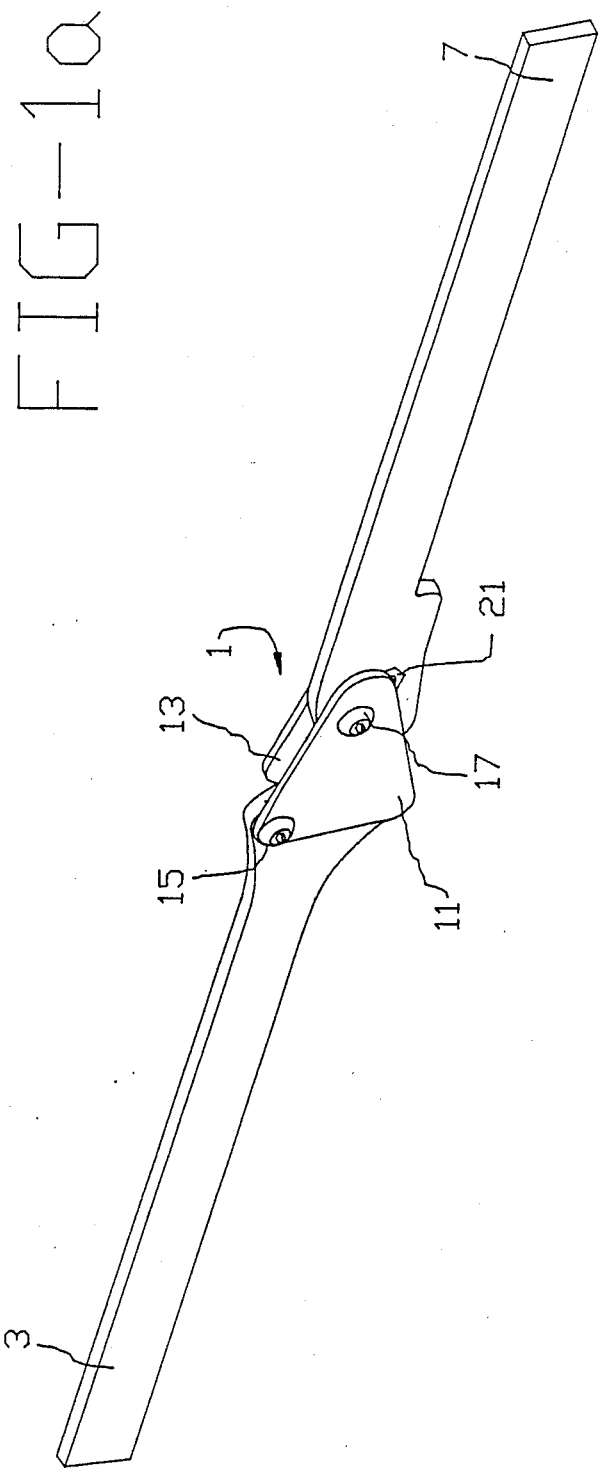

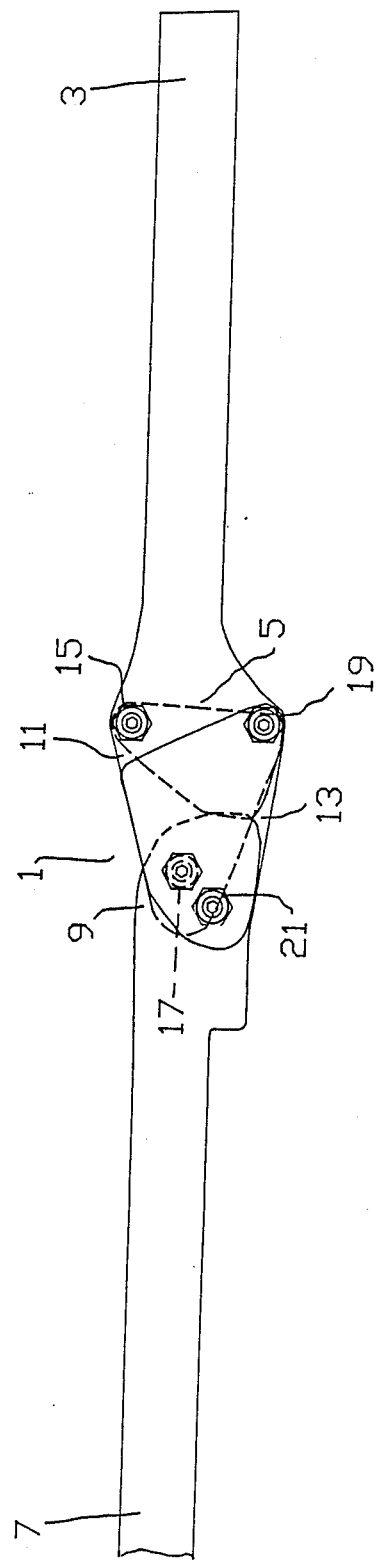

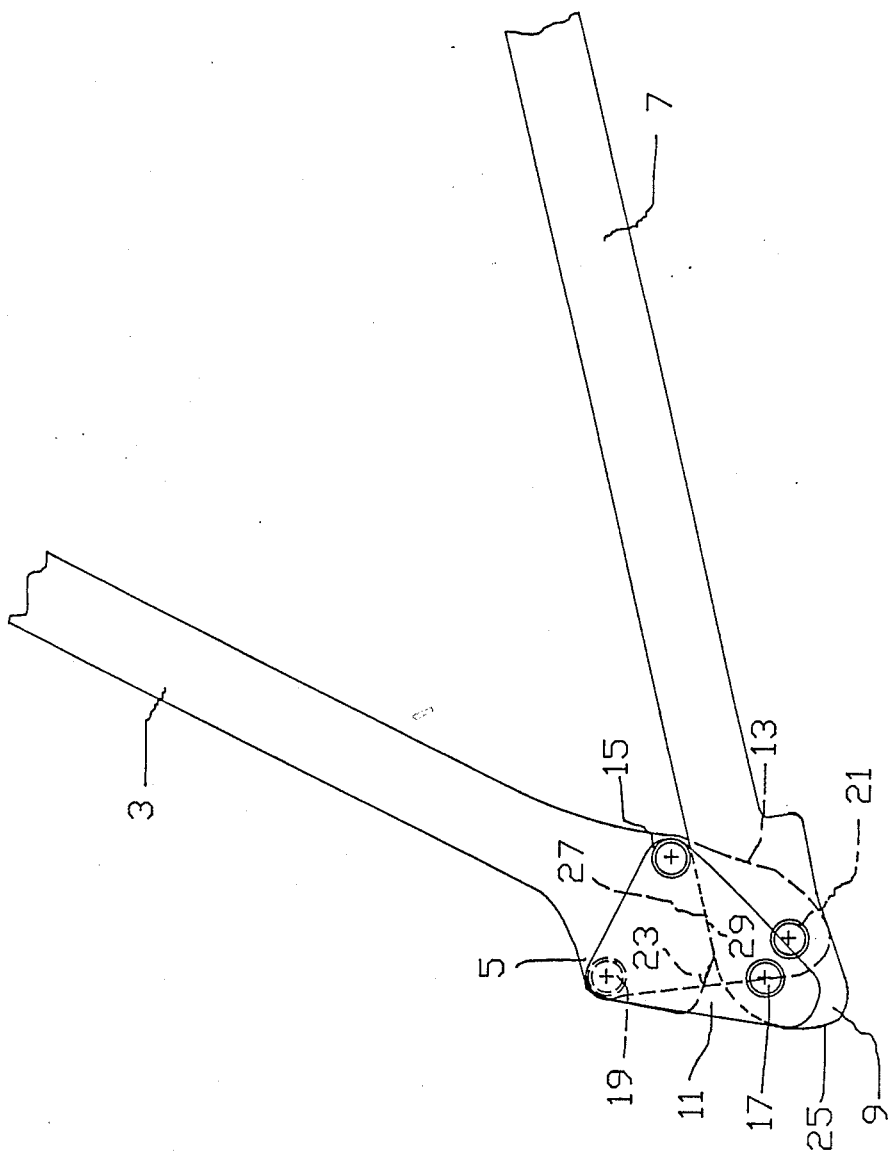

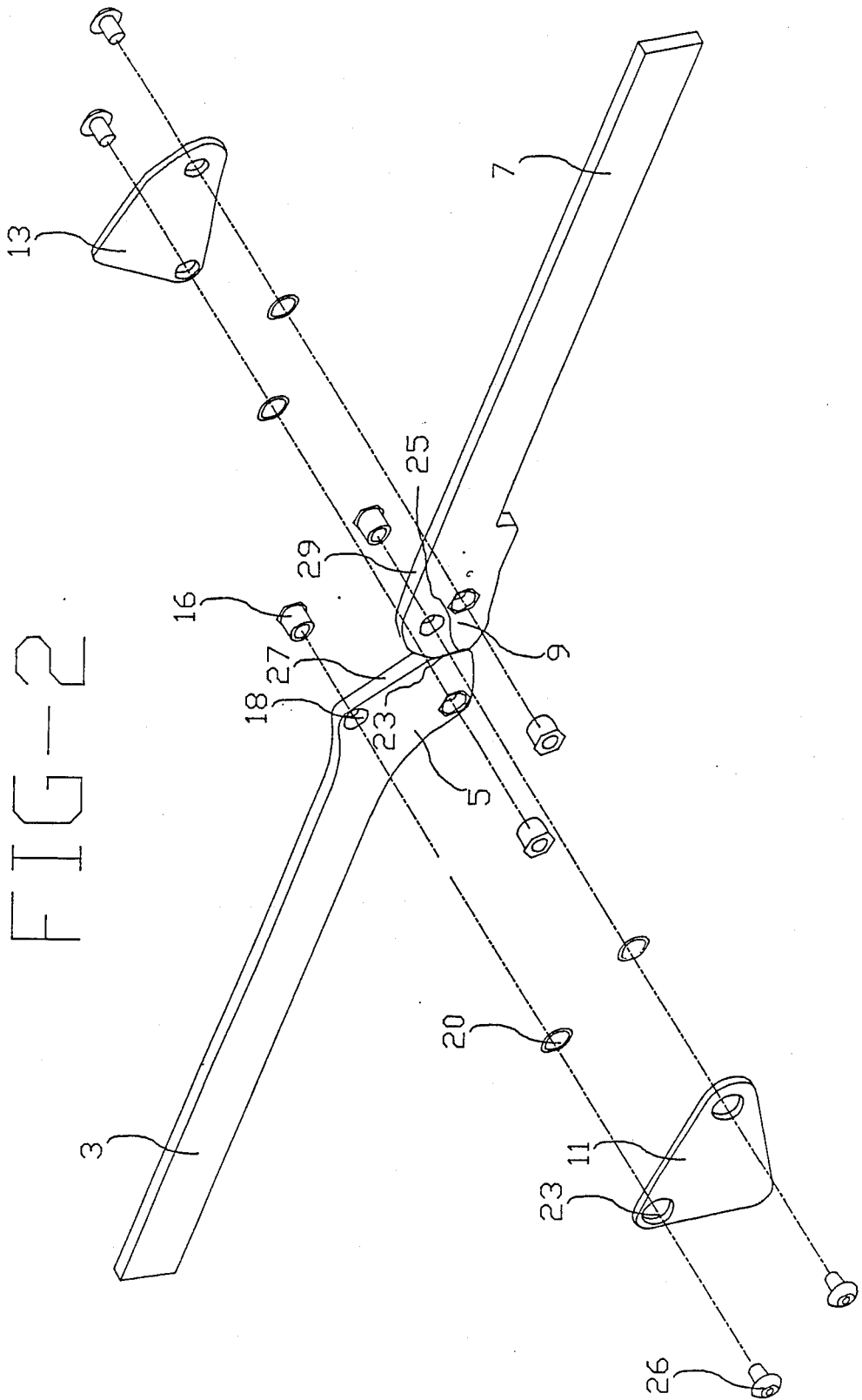

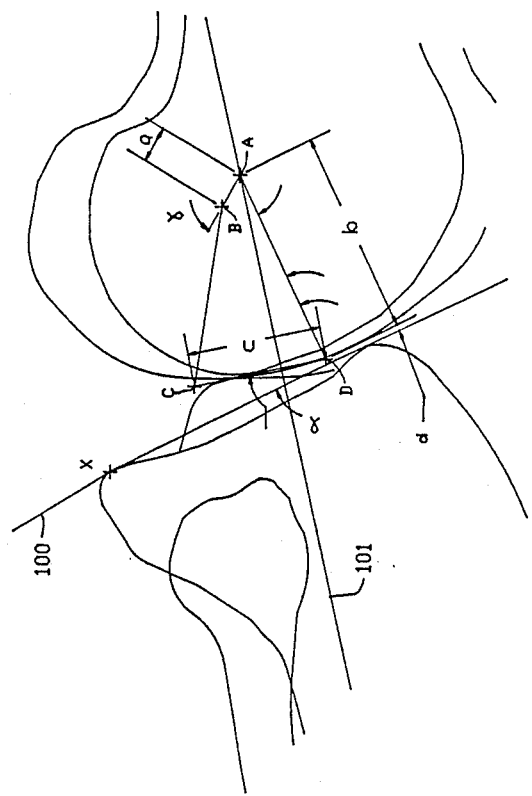

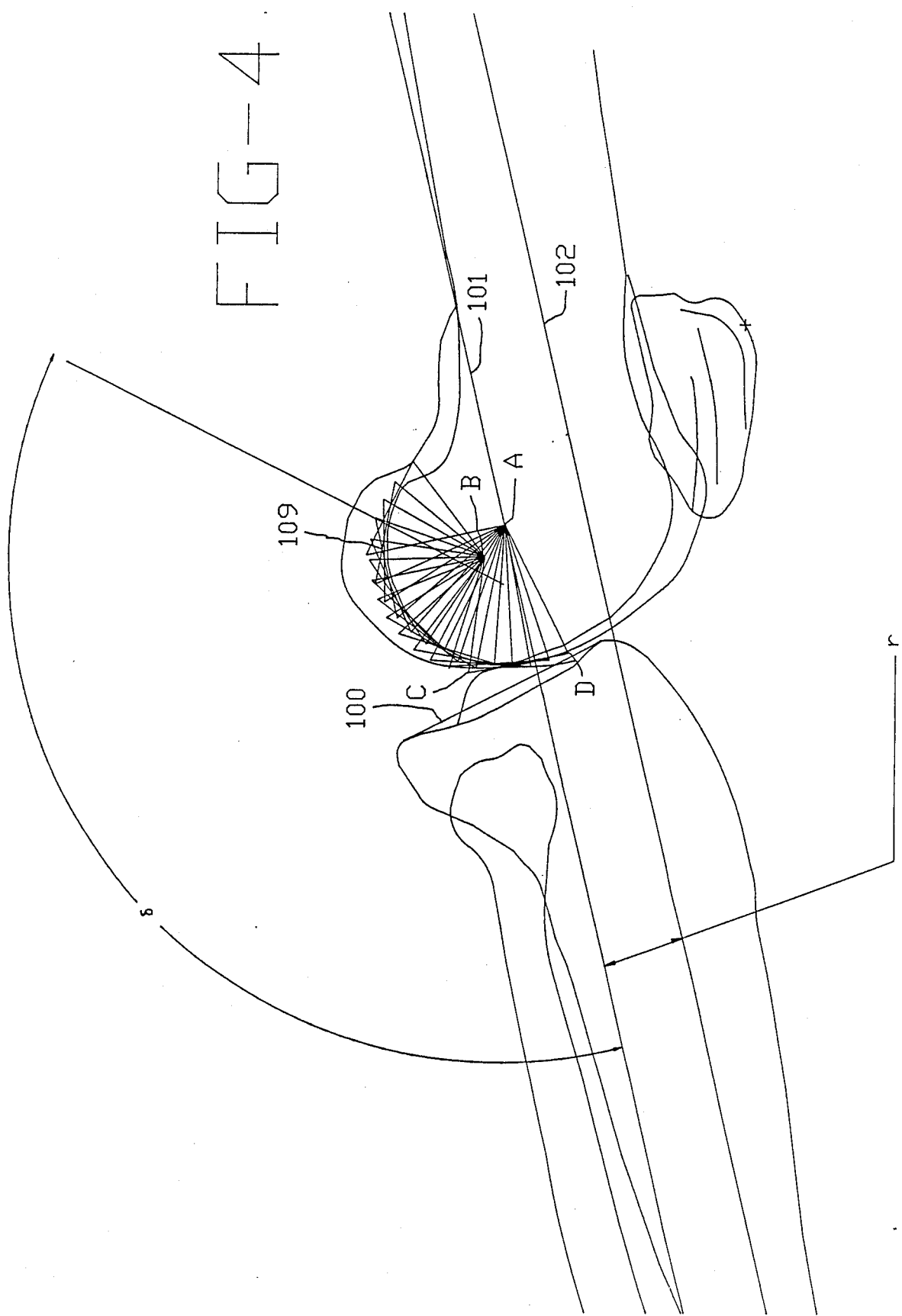

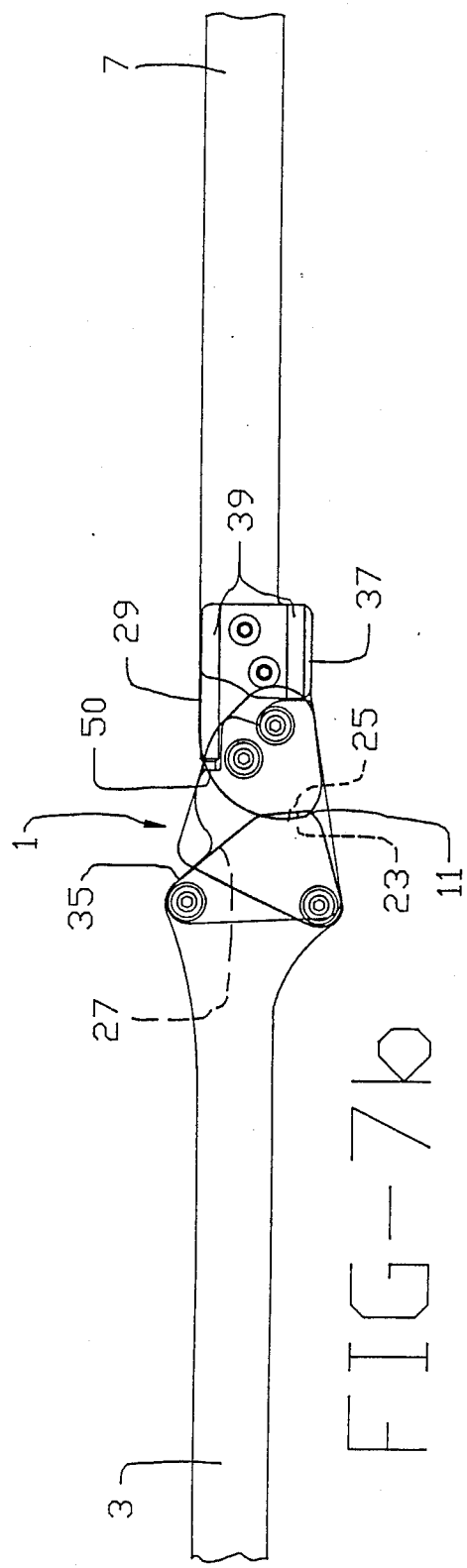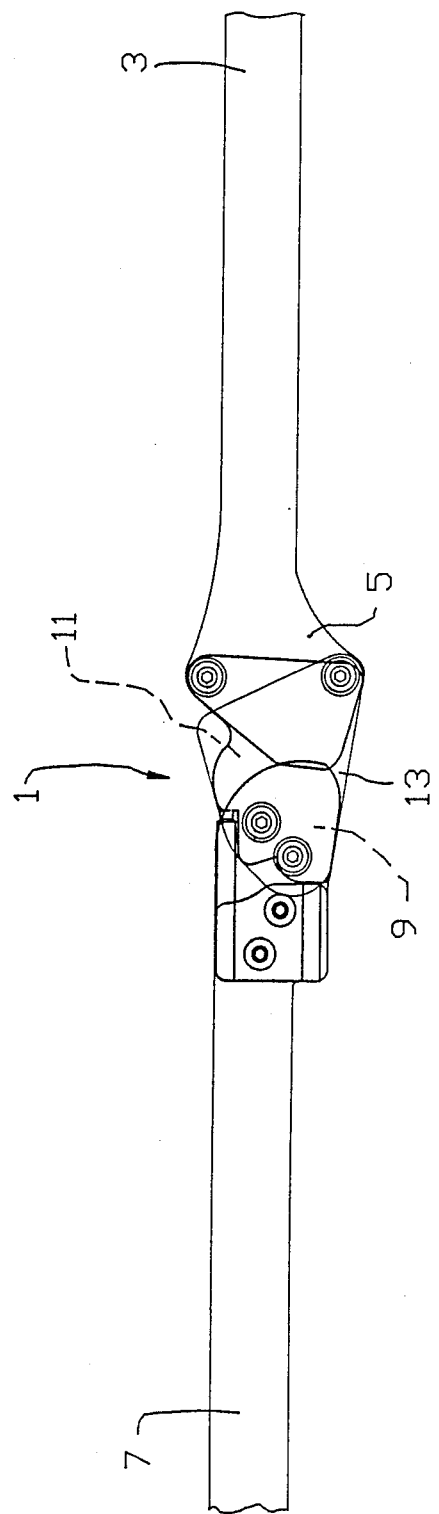
FIG-7b
FIG-7c

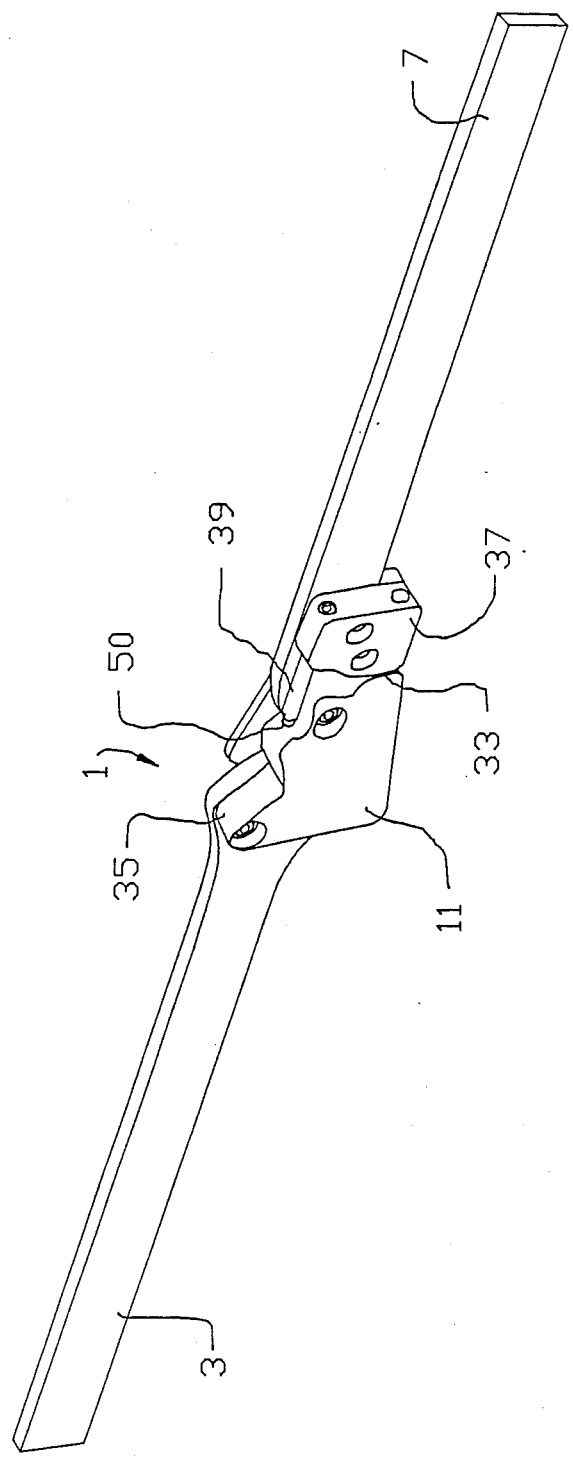

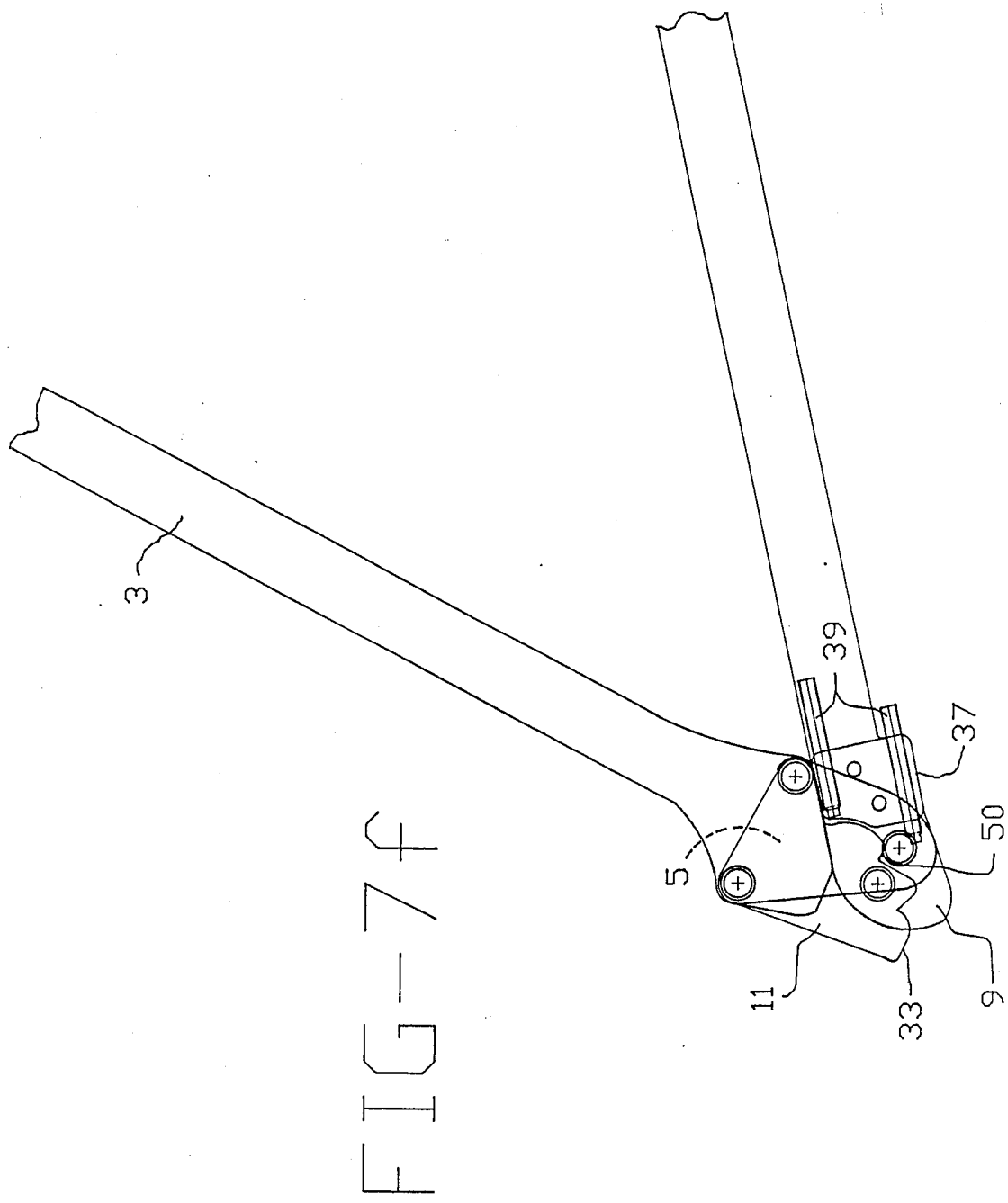

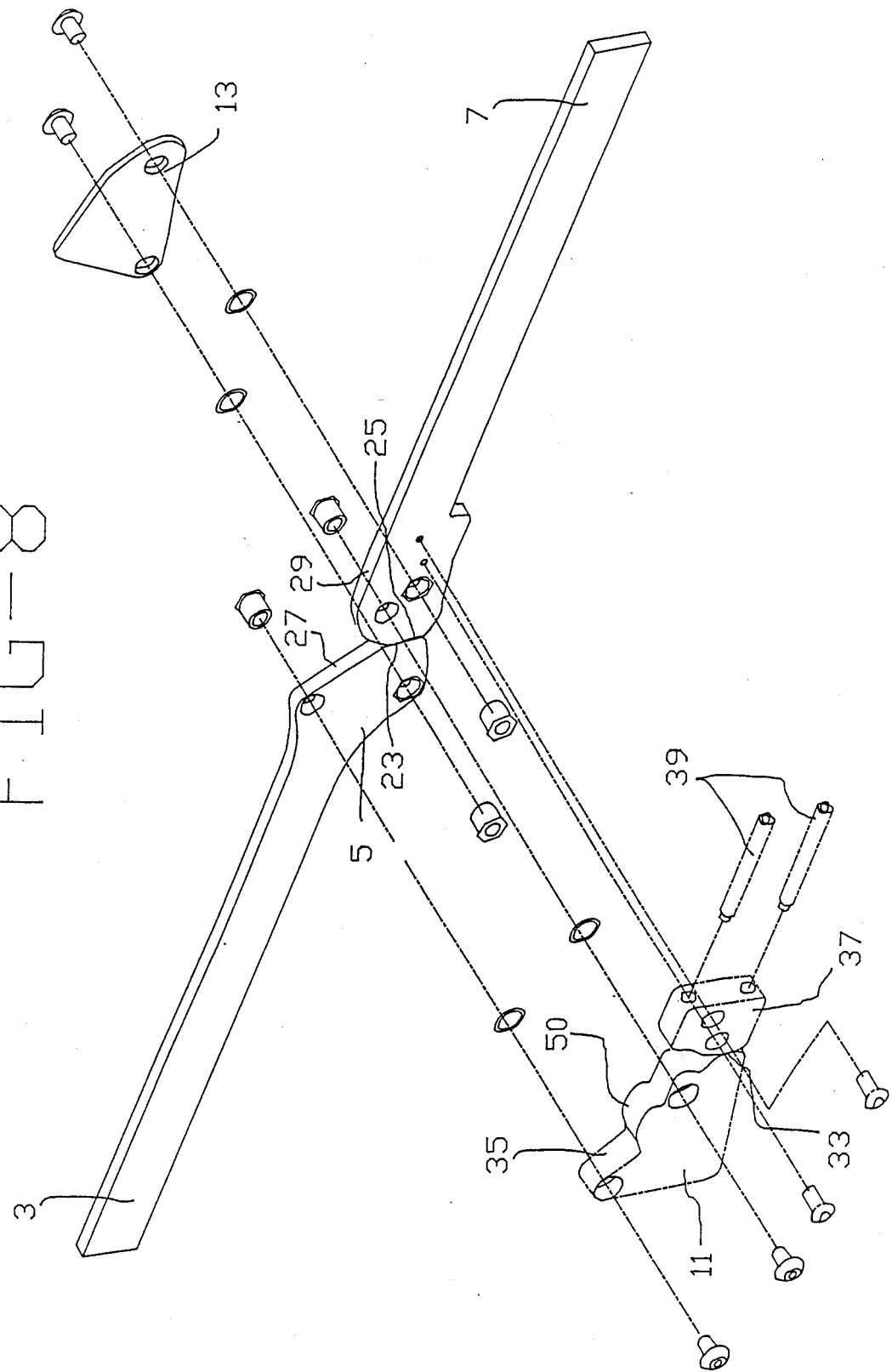

MECHANICAL ARTICULATED JOINT FOR KNEE BRACES

BACKGROUND OF THE INVENTION

1. Field of the Invention:

The present invention relates to a new articulated mechanical joint for use, in particular but not exclusively, in knee braces intended to reinforce an injured knee joint particularly during convalescence or permanently in the case of a weak joint. Such braces are also used by athletes to prevent knee injuries.

2. Brief Description of the Prior Art:

The thigh and leg of the human body are articulated to each other through the knee joint of which the principal motions are extension and flexion by rotation about a horizontal axis extending across the knee in a medial-lateral direction. These motions are complex as they take place about a rotation axis which is not fixed, as in the elbow, but shifts slightly across the knee in an anterior-posterior direction. It is important, for an adequate knee brace, to follow the shifting path of the rotation axis of the knee as closely as possible. Additionally, and particularly in the case of injured or weak knees, means must be provided in the artificial joint of the brace, to control extension of the knee joint and usually stop it short of 15° to 5° of full extension. It is indeed in this range that important knee ligament injuries occur.

Another type of rotation is one that takes place about a further horizontal axis which extends in an anterior-posterior direction, that is tranverse to the plane of extension and flexion. This motion may give rise, in an injured or weak knee, also to severe knee ligament injuries. An appropriate knee brace should consequently protect the knee against sidewise motion about this further horizontal axis, both during extension and flexion motions and this protection should not interfere with the latter motions.

The patent and scientific literature is replete with proposals for knee braces including a mechanical joint pivoting about a single fixed axis or a somewhat movable axis which cannot move parallel to the complex motion of the knee. Nor does any provision available control extension fully adequately and adjustably so that the latter will not exceed a predetermined limit, usually within the 15° to 5° short of full extension, as noted above, where ligament and muscle injuries are mostly experienced. It seems also that while much attention has been given to firmly securing the links to the mechanical joint, pivoted together at one end, to the corresponding thigh and leg, less attention is given to the pivot joint itself coupling the links. The pivot joint however is the main component of the knee brace as it is the one that transmits the full loads between the thigh and the leg. Lack of adequate sturdiness in this pivot joint consequently gives rise to possible dangerous sidewise motions during flexion and extension.

OBJECTS OF THE INVENTION

It is therefore a principal object of the invention to provide an improved mechanical articulated joint for a knee brace that is devoid of the above weaknesses by more accurately following the complex motion of the knee joint.

Another object of the invention is to provide a joint construction capable of more adequately protecting the knee against sidewise motions.

A further object of the present invention lies in providing a small, non-cumbersome mechanical articulated joint of simple design and having little weight.

Still another object of the present invention is to provide an articulated mechanical joint which can be used in different knee apparatuses, such as knee braces of the above defined type, artificial articulated knees of leg prostheses, and the like.

SUMMARY OF THE INVENTION

More specifically, in accordance with the invention, there is provided an articulated mechanical joint for a knee apparatus applied to a human wearer and selected from the group consisting of a knee brace allowing extension and flexion of the wearer's knee to which the brace is applied, an artificial articulated knee of a leg prosthesis, and the like, which mechanical joint comprises:

a femoral link having a pivot end and a tibial link also having a pivot end, the two pivot ends adjoining one another and lying in a common plane generally perpendicular to the rotation axis of the knee;

a first plate and a second plate; which plates lying flatly over the femoral and tibial links in overlapping relation with the adjoining pivot ends, each plate being located on one side of the links;

first means pivotally mounting the first plate to the pivot end of the femoral link; second means pivotally mounting the first plate to the pivot end of the tibial link; third means pivotally mounting the second plate to the pivot end of the femoral link; and fourth means pivotally mounting the second plate to the pivot end of the tibial link; and extension stop means preventing extension of said femoral and tibial links beyond a predetermined extension limit.

In full extension of the knee, (a) the first pivot means has a first pivot axis perpendicular to the above-mentioned common plane and intersecting a first, straight line located in this common plane posteriorly to a second line parallel to the first line and defined in the common plane by a medial-lateral transversal plane intersecting both centrally of the femoral head and tibial malleolus of the wearer, (b) the second pivot means has a second pivot axis both perpendicular to the above defined common plane and anterior to the first line, (c) the third pivot means has a third pivot axis both perpendicular to the common plane and posterior to the first line, and (d) the fourth pivot means has a fourth pivot axis both perpendicular to the common plane and posterior to the first line.

Preferably, the articulated joint further comprises flexion stop means preventing flexion of the femoral and tibial links beyond a predetermined flexion limit.

In accordance with a preferred embodiment of the invention, the extension and flexion stop means comprise the pivot ends formed with terminal edges, the extension stop means comprising the terminal edges formed with anterior portions butting against one another when the femoral and tibial links have reached the predetermined extension limit, and the flexion stop means comprising the terminal edges formed with posterior portions butting against one another when the femoral and tibial links have reached the predetermined flexion limit.

In accordance with another preferred embodiment of the articulated joint of the present invention, one of the first and second plates is an outer plate formed, along a peripheral edge thereof facing one of the femoral and tibial links, with an anterior stop land and a posterior stop land located rearwardly of the anterior stop land; and the extension and flexion stop means comprise the anterior and posterior stop lands, a block solid with the said one link on the outer face thereof, and a pair of screws threadable through the block in the direction of the stop lands, respectively, which screws each having a free end butting on the corresponding anterior or posterior stop land to prevent extension and flexion of the femoral and tibial links beyond the extension and flexion limits.

Other objects, advantages and features of the invention will appear from the description that follows of preferred embodiments thereof adapted for use, as a non limitative example, in a knee brace, which description is given with reference to the appended drawings.

BRIEF DESCRIPTION OF THE DRAWINGS

FIG. 1a is a perspective view of a mechanical articulated joint made according to the teaching of the present invention and FIGS. 1b, 1c, 1d, 1e, 1f, are, respectively, an external elevation view of the joint in extension; an internal elevation view; a top plan view; a partial enlarged scale plan view; and a view similar to FIG. 1b but showing the joint in full flexion;

FIG. 2 is an exploded view of the joint of FIG. 1;

FIG. 3 shows, in full extension of the wearer's knee, the respective positions of the four pivot axes of the articulated joint of FIG. 1;

FIG. 4 is a diagrammatic illustration of the variation in respective position of the four pivot axes of the joint of FIG. 1, and of the position of these axes with respect to the femur of the wearer, during rotation of the articulated joint and wearer's knee;

FIGS. 7a to 7f are views similar to FIGS. 1a to 1f but of another embodiment of the articulated joint according to the invention; and FIG. 8 is an exploded view of the joint of FIG. 7.

DESCRIPTION OF THE PREFERRED EMBODIMENTS

Referring to FIGS. 1 and 2, there is shown a mechanical articulated joint 1 for a knee brace allowing extension and flexion of a wearer's knee to which the brace is to be applied. The joint shown is for application on the lateral side of the leg while a like but geometrically reversed joint (not shown) is applied to the medial side.

Figure 1B:
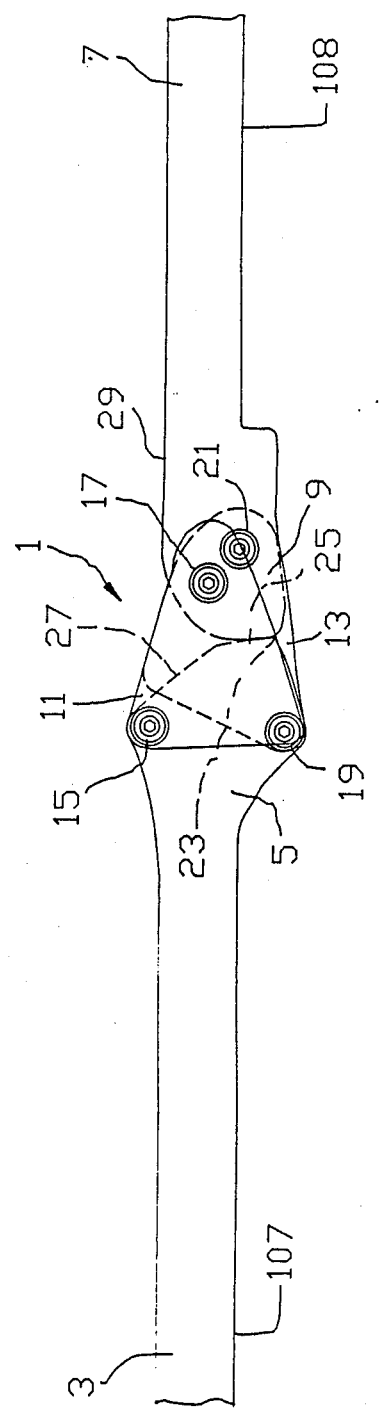
Figure 1D:
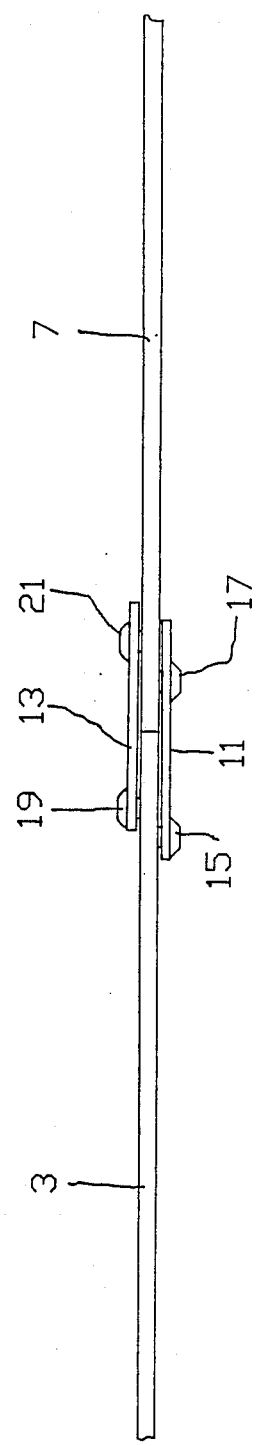
Figure 1E:
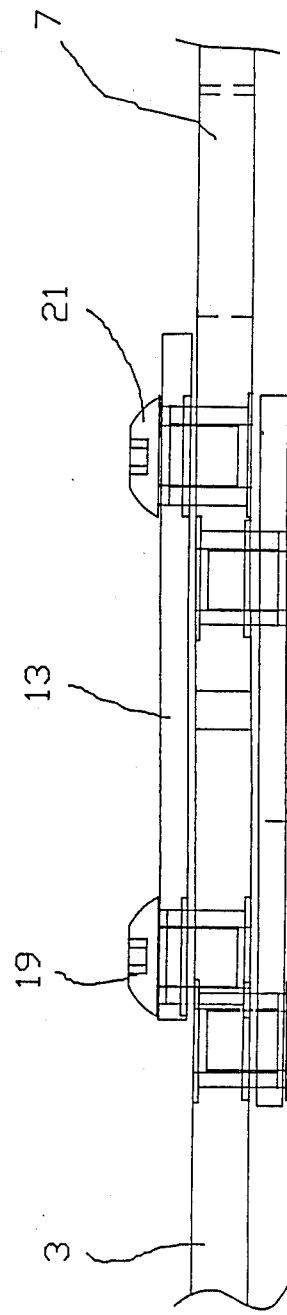

The joint 1 comprises an elongated tibial link 3 having a pivot end 5 and an elongated femoral link 7 likewise having a pivot end 9; the two pivot ends 5 and 9 being both flat and coplanar, and adjoining one another in assembled condition of the joint 1. Assembly is through an outer cheek, flat plate 11 and an inner cheek, flat plate 13 both lying flatly over the links 3, 7, in overlapping relation with the pivot ends 5, 9. It can also be appreciated that the plates 11 and 13 provide resistance to sidewise motion of the tibia and femur of the leg. Referring to FIGS. 1b and 1c, a first dowel pivot 21 mounts the inner plate 13 to the pivot end 9 of the femoral link 7 and a second dowel pivot 19 mounts it on the pivot end 5 of the tibial link 3. A third dowel pivot 17 similarly mounts the outer plate 11 to the pivot end 9 of the femoral link 7 while a fourth dowel pivot 15 mounts the outer plate 11 to the pivot end 5 of the tibial link 3. Although the pivot joint 1 is shown in FIGS. 1a to 1e in fully extended condition, it should be pointed out that, in practice, the joint 1 is in most of the cases prevented to extend fully by stop means to be described hereinafter.

All dowel pivots are alike so that only one need be described which will be the dowel pivot 15 of FIG. 2. It comprises an inwardly threaded shouldered dowel 16 rotatably mounted in a hole 18 of the tibial link 3 and receiving a screw 26 extending successively through a hole 23 of the plate 11 and through a washer 20. The outer plate 11 may thus be held flatly against the outer face of the tibial link 3, by threading screw 26 into the dowel 16, while allowing relative rotation of the plate 11 and link 3. Any other suitable pivot devices may of course be used.

As illustrated in FIGS. 1b and 1f, the pivot ends 5 and 9 are formed with terminal edges facing one another and butting against one another when the links 3 and 7 have reached a predetermined extension limit, usually short of full extension by about 15° to 5°, as aforesaid, and also butting against one another when the links 3 and 7 have reached a predetermined flexion limit which is about 128° away from full extension.

More specifically, the terminal edges of the pivot ends 5 and 9 have anterior portions 23, 25, and posterior portions 27, 29. The anterior portions 23, 25, butt against one another when the links 3 and 7 are at the predetermined limit of extension, while the posterior portions 27, 29 butt against one another when the femoral and tibial links have reached the desired limit of flexion. As can be appreciated, the angles formed by the tibial and femoral links 3 and 7, in maximal extension and in maximal flexion, may be controlled by changing the configuration of the anterior and posterior portions 23, 25, 27, 29. Thus, the prescribing physician may select the limit of extension and/or flexion suitable for any specific situation.

In FIGS. 1b and 1c, the anterior portions 23 and 25 are illustrated as overlapping one another instead of abutting against each other. This is to show full extension of the articulated joint 1 corresponding to full extension of the wearer's knee. This also shows that, in practice, the articulated joint 1 is, in most of the cases, prevented to fully extend, that is usually short of full extension by about 15° to 5°, as stated hereinabove.

Figure 5:
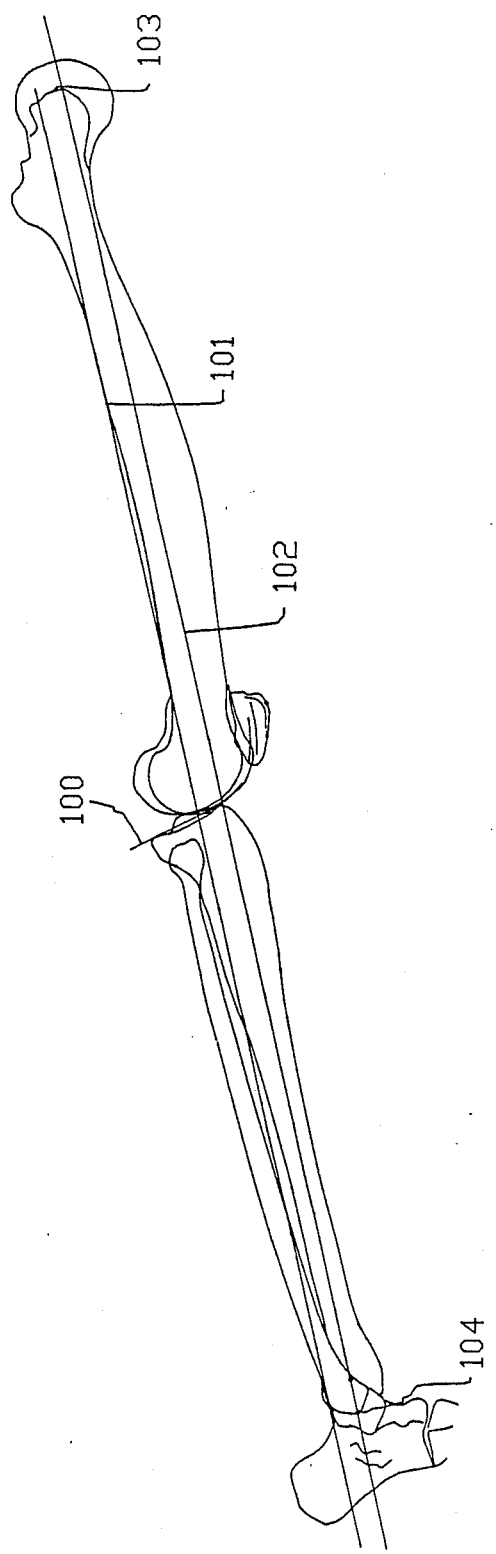
FIGS. 5 and 6 show how the joint of FIG. 1 is positioned on the knee of the wearer.

FIG. 3 gives the geometrical relationship between the pivot axes A, B, C and D, respectively corresponding to the above defined dowel pivots 21, 17, 15 and 19 of FIG. 1b, when the links 3 and 7 are in full extension of the knee, it being reminded that the links 3 and 7 are in practice stopped slightly short of full extension by the butting anterior portions 23, 25. The positions of the axes A, B, C, D are given in FIG. 3 with reference to a straight line 100 defined in the common plane of the pivot ends 5 and 9 by the medial tibial plateau (MTP) of the wearer, and also with reference to a line 101 located in the same plane. This line 101 is a straight line parallel to another line 102 defined in the common plane of the pivot ends 5 and 9 by a medial-lateral transversal plane intersecting both centrally of the femoral head 103 and tibial malleolus 104 of the wearer, as illustrated in FIG. 5. The distance r (FIG. 4) between the two parallel lines 101 and 102 is about 0.722 inch. The angles and dimensions are, in FIG. 3, as follows, it being reminded that the pivot axis A intersects the line 101:

a≅0.31 inch
b≅1.25 inch
c≅0.90 inch
d≅0.030 inch
α≅89°
β≅74°
γ≅58°

Figure 6:
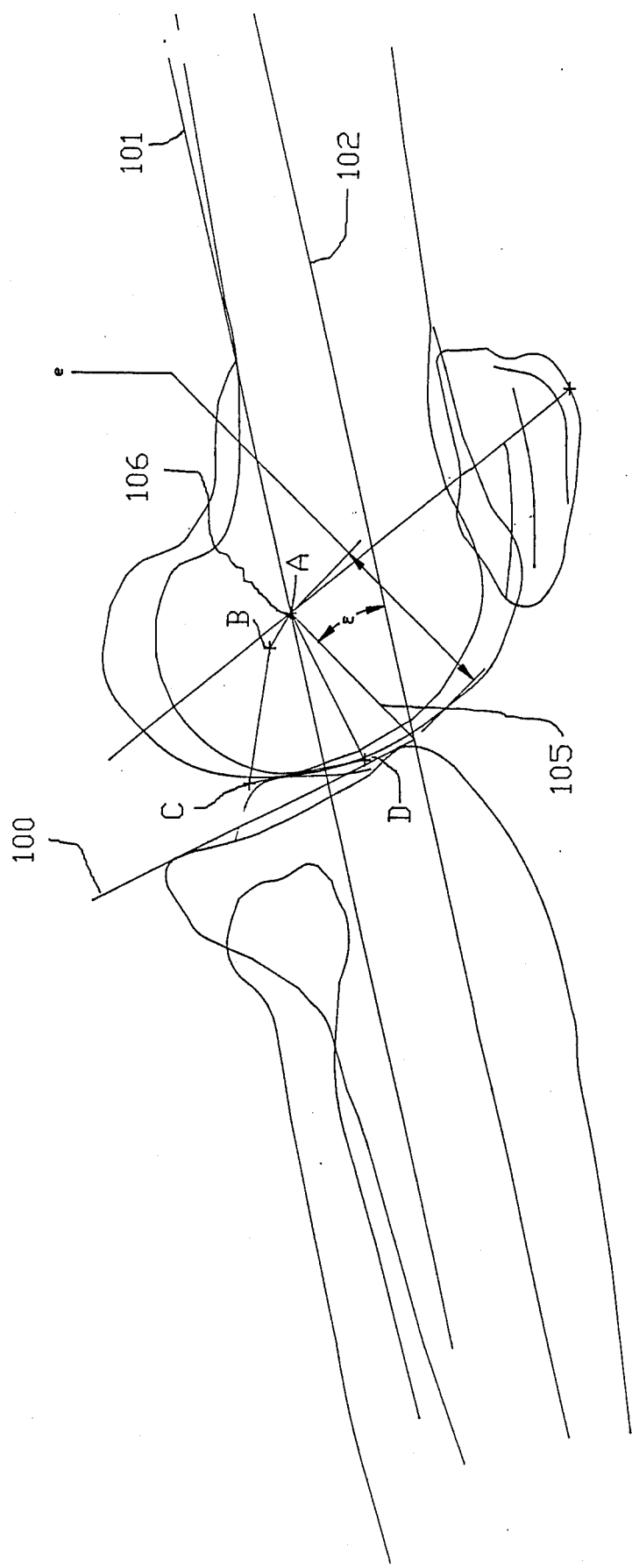
Figure 7D:
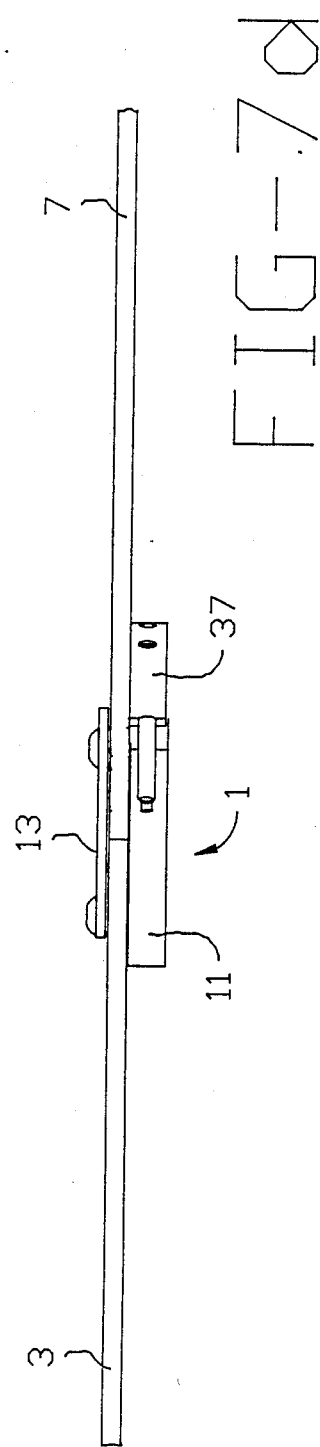
Figure 7E:
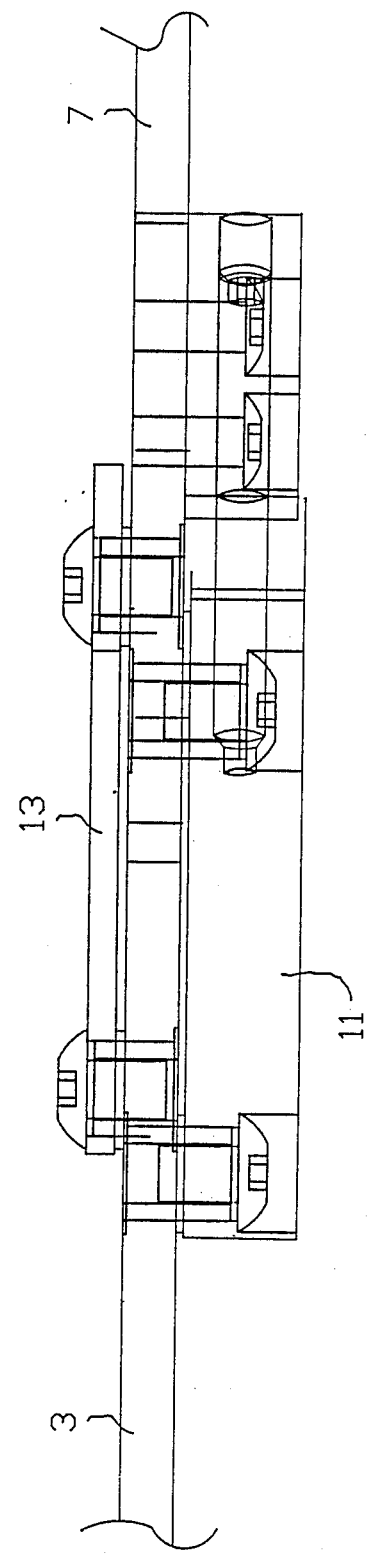

The following procedure can be used to facilitate positionment of the articulated joint 1 on the wearer's knee. Firstly, with the wearer's knee fully extended as illustrated in FIG. 6, the locations of the straight lines 100, 101 and 102 are determined. Then, a point 106 corresponding to the position of the pivot axis A is located, using a line 105 (FIG. 6) coplanar with the lines 100, 101 and 102, traversing the intersection between the lines 100 and 102, and defining with the line 102 an angle ω of 32° centered on the intersection between the lines 100 and 102. The intersection between the lines 101 and 105 defines the point 106, that is at a distance e of about 1.348 inch from the intersection between the lines 100 and 102.

After point 106 has been located, one has only to align the anterior edges 107 and 108 (FIG. 1b) of the links 3 and 7 with the line 101, with the axis A of the pivot 21 passing through the point 106. The joint 1 is thereby easily positioned on the wearer's knee.

As evidenced in FIG. 4, during extension and flexion of the joint 1 (from full extension to the maximum flexion angle δ=128° of the joint 1), the axis of rotation of the links 3 and 7 is shifted. The positions of the dowel pivots 15, 17, 19 and 21 are so selected that the latter rotation axis is so shifted that the straight line interconnecting the pivot axes C and D in the common plane of the pivot ends 5 and 9 follows tangentially the contour 109 of the medial, smaller femoral condyle, to reproduce accurately the complex rotation of the wearer's knee as illustrated in FIG. 4.

The above dimensions and eventually the above angles given with reference to FIGS. 3, 4, 5 and 6, can be slightly changed for adaptation to patients having femur and tibia of different dimensions and shape (for example adults and children have femur and tibia of different dimensions).

Additional stop means may be provided for limiting extension and flexion between the preselected extension limit determined by the butting anterior portions 23 and 25 (which may be full extension where the knee brace is for use on a healthy knee as with athletes) and full flexion. One such additional stop means is shown in FIGS. 7a to 7f and 8. Of course, the elements of the articulated joint of FIGS. 7a to 7f, and 8 corresponding to elements of the joint 1 of FIG. 1a to 1f, and 2 are identified by the same reference numerals.

As shown, the joint 1 in this case is of the same design as that in FIGS. 1a to 1f, and 2 except that the outer plate 11 is substantially thicker, and formed, along its peripheral edge facing the link 7, with an anterior stop land 33 and a posterior stop land 35 located rearwardly of land 33 in the direction of flexion. The stop means comprise a block 37 integral with the link 7, on its outer face, and a pair of screws 39 which are advantageously of the Allen type. The screws 39 are threadable through the block 37 in the direction of the stop lands 33, 35, respectively. As can easily be gathered from FIGS. 7b and 7f, particularly, adjustment of the screws 39 with respect to their respective lands 33, 35, automatically controls the extend of the extension and flexion of the joint 1.

The aforesaid anterior portions 23, 25, and posterior portions 27, 29 of the terminal edges of the links 3, 7 can serve to determine maximal extension and flexion of the links 3, 7, which can be full extension and flexion, while the additional stop means 33, 35, 37, 39, serve to set an extension limit short of maximal extension and a flexion limit also short of maximal flexion.

As an example, FIG. 7f shows adjustment of the screws 39 for maximal flexion of the articulated joint 1, and for an extension limit short of maximal extension.

As another example, FIG. 7b shows adjustment of the screws 39 to lock the joint 1. For that purpose, the lower screw 39 (FIG. 7b) is adjusted to allow maximal extension while the upper screw 39 (FIG. 7b) is adjusted to cooperate with an intermediate stop land 50 of the plate 11 to prevent flexion of the articulated joint 1.

Of course, the joint 1 may only be provided with the first stop means 23, 25, 27, 29 the attending physician selecting the appropriate terminal edges configurations, as mentioned before.

The links 3, 7 are secured to the leg and thigh of a patient by any fastening means known to the specialist in this field to ensure unweavering holding. An example of such fastening means are described in Canadian Pat. No. 1.201.951 to CHARUEST, issued on Mar. 18th, 1986. Of course, in order to adjust the joint 1 on the thigh and leg of a patient, the links 3 and 7 can be bent as required, keeping in mind that the flat pivot ends 5, 9 and plates 11, 13 must remain generally perpendicular to the shifted axis of rotation of the knee.

In the above description, the preferred embodiments of the articulated joint of the invention have been described in relation to an application to a knee brace. However, the invention should not be limited to such an application. Indeed, the articulated mechanical joint can also be used in combination with, for example, the articulated, artificial knee of a leg prosthesis replacing an amputated limb, and with other orthopedic apparatuses, or the like.

Although the present invention has been described hereinabove by means of preferred embodiments thereof, it should be pointed out that any modification to these preferred embodiments, within the scope of the appended claims, is not deemed to change or alter the concept and nature of the subject invention.

What is claimed is:

1. An articulated mechanical joint for a knee apparatus applied to a human wearer and selected from the group consisting of a knee brace allowing extension and flexion of the wearer's knee to which said brace is applied, an artificial articulated knee of a leg prosthesis, said joint comprising:

a femoral link having a pivot end and a tibial link also having a pivot end, said pivot ends adjoining one another and lying in a common plane generally perpendicular to the rotation axis of the knee;

a first plate and a second plate; said plates lying flatly over said links in overlapping relation with said adjoining pivot ends, each plate being located on one side of said links;

first means pivotally mounting said first plate to the pivot end of said femoral link; second means pivotally mounting said first plate to the pivot end of said tibial link; third means pivotally mounting said second plate to the pivot end of said femoral link; and fourth means pivotally mounting said second plate to the pivot end of said tibial link; and extension stop means preventing extension of said femoral and tibial links beyond a predetermined extension limit;

wherein, in full extension of the knee, (a) said first pivot means has a first pivot axis perpendicular to said common plane and intersecting a first, straight line located in said common plane posteriorly to a second line parallel to said first line and said second line being defined in said common plane by a medial-lateral transversal plane intersecting both centrally of the femoral head and tibial malleolus of the wearer, (b) said second pivot means has a second pivot axis both perpendicular to said common plane and anterior to said first line, (c) said third pivot means has a third pivot axis both perpendicular to said common plane and posterior to said first line, and (d) said fourth pivot means has a fourth pivot axis both perpendicular to said common plane and posterior to said first line.

2. An articulated joint as defined in claim 1, wherein said pivot ends of the femoral and tibial links are flat, and wherein said first and second plates are also flat.

3. An articulated joint as defined in claim 1, wherein said extension stop means comprises said pivot ends formed with terminal edges which butt against one another when said femoral and tibial links have reached said predetermined extension limit.

4. An articulated joint as defined in claim 1, in which one of said first and second plates is an outer plate, and in which said outer plate is formed, along a peripheral edge thereof facing one of said femoral and tibial links, with a stop land; and said extension stop means comprises said stop land, a block integral with said one link on the outer face thereof, and a screw threadable through said block in the direction of said stop land to adjust said extension limit, said screw having a free end butting against the stop land to prevent extension of the femoral and tibial links beyond the so adjusted extension limit.

5. An articulated joint as defined in claim 1, wherein, in full extension of the knee, said third pivot axis is lower than said first pivot axis, and said second and fourth pivot axes are substantially of the same height.

6. An articulated joint as defined in claim 1, in which the distance between the first and third pivot axes is substantially smaller than the distance between the second and fourth pivot axes.

7. An articulated joint as defined in claim 1, wherein, in full extension of the knee:
the first and second lines in said common plane are separated by a distance of about 0.722 inch;
the medial tibial plateau of the wearer defines in said common plane a third, straight line intersecting said second line;
a fourth, straight line located in said common plane and interconnecting the intersection between the second and third lines with the first pivot axis is about 1.348 inch long and defines with said second line an angle of about 32° centered on the intersection between the second and third lines;
a fifth, straight line located in said common plane and interconnecting the first and second pivot axes is about 1.125 inch long and defines with the third line an angle of about 89°;
a sixth, straight line located in said common plane and interconnecting the first and third pivot axes is about 0.31 inch long and defines with said fifth line an angle of about 58° centered on said first pivot axis; and
a seventh, straight line located in said common plane and interconnecting the second and fourth pivot axes is about 0.90 inch long and defines with said fifth line an angle of about 74° centered on said second pivot axis.

8. An articulated joint as defined in claim 1, further comprising means for locking said articulated mechanical joint at said predetermined extension limit of the femoral and tibial links.

9. An articulated joint as defined in claim 8, in which one of said first and second plates is an outer plate, and in which said outer plate is formed, along a peripheral edge thereof facing one of said femoral and tibial links, with a stop land; and said joint locking means comprises said stop land, a block integral with said one link on the outer face thereof, and a screw threadable through said block in the direction of said stop land in order to butt a free end of the screw against the stop land so as to lock said articulated joint at said predetermined extension limit of said femoral and tibial links.

10. An articulated joint as defined in claim 1, further comprising flexion stop means preventing flexion of said femoral and tibial links beyond a predetermined flexion limit.

11. An articulated joint as defined in claim 10, wherein said flexion stop means comprises said pivot ends formed with terminal edges which butt against one another when said femoral and tibial links have reached said predetermined flexion limit.

12. An articulated joint as defined in claim 10, wherein said extension and flexion stop means comprise said pivot ends formed with terminal edges, said extension stop means comprising said terminal edges formed with anterior portions butting against one another when said femoral and tibial links have reached said predetermined extension limit, and said flexion stop means comprising said terminal edges formed with posterior portions butting against one another when said femoral and tibial links have reached said predetermined flexion limit.

13. An articulated joint as defined in claim 10, in which one of said first and second plates is an outer plate, and in which said outer plate is formed, along a peripheral edge thereof facing one of said femoral and tibial links, with a stop land; and said flexion stop means comprises said stop land, a block integral with said one link on the outer face thereof, and a screw threadable through said block in the direction of said stop land to adjust said flexion limit, said screw having a free end butting against the stop land to prevent flexion of the femoral and tibial links beyond the so adjusted flexion limit.

14. An articulated joint as defined in claim 10, wherein one of said first and second plates is an outer plate, and wherein said outer plate is formed, along a peripheral edge thereof facing one of said femoral and tibial links, with an anterior stop land and a posterior stop land located rearwardly of said anterior stop land; and said extension and flexion stop means comprise said anterior and posterior stop lands, a block integral with said one link on the outer face thereof, a first screw threadable through said block in the direction of the anterior stop land to adjust said extension limit and a second screw threadable through said block in the direction of said posterior stop land to adjust said flexion limit, said first screw having a free end butting against the anterior stop land to prevent extension of the femoral and tibial links beyond the so adjusted extension limit, and said second screw having a free end butting against the posterior stop land to prevent flexion of said femoral and tibial links beyond the so adjusted flexion limit.

15. An articulated joint as defined in claim 14, wherein said outer plate is said second plate, and said one link is said femoral link.

16. An articulated joint as defined in claim 1, wherein, in full extension of the knee:
   the ratio between (a) the distance between the first and third pivot axes and (b) the distance between the first and second pivot axes is about 0.248; and
   the ratio between (a) the distance between the first and third pivot axes and (b) the distance between the second and fourth pivot axes is about 0.344.

17. An articulated joint as defined in claim 16, in which, in full extension of the knee:
   a third, straight line interconnecting in said common plane the first and second pivot axes defines with a fourth, straight line interconnecting in said common plane the first and third pivot axes an angle of about 58° centered on said first pivot axis; and
   a fifth, straight line interconnecting in said common plane the second and fourth pivot axes defines with said third line an angle of about 74° centered on said second pivot axis.

18. An articulated joint as defined in claim 17, in which the ratio between (a) the distance between the first and third pivot axes and (b) the distance between the parallel first and second lines is about 0.43.

19. An articulated joint as defined in claim 17, wherein, in full extension of the knee:
   the medial tibial plateau defines in said common plane a sixth, straight line intersecting with said second line;
   a seventh, straight line located in said common plane and interconnecting the first pivot axis with the intersection of the second and sixth lines, defines with said second line an angle of about 32° centered on said intersection of the second and sixth lines; and
   the sixth line defines with the third line an angle of about 89°.

20. An articulated joint as defined in claim 19, in which the ratio between (a) the distance between the first and third pivot axes and (b) the distance between the first pivot axis and the intersection between the second and sixth lines is about 0.23.

* * * * *